US005656207A

United States Patent [19]
Woodhead et al.

[11] Patent Number: 5,656,207
[45] Date of Patent: Aug. 12, 1997

[54] DETECTING OR QUANTIFYING MULTIPLE ANALYTES USING LABELLING TECHNIQUES

[75] Inventors: James Stuart Woodhead; Ian Weeks; Shariar Batmanghelich, all of Cardiff, United Kingdom

[73] Assignee: Gen Probe Incorporated

[21] Appl. No.: 439,311

[22] Filed: May 11, 1995

Related U.S. Application Data

[63] Continuation of Ser. No. 781,182, May 26, 1992, abandoned.

[30] Foreign Application Priority Data

Jun. 24, 1989 [GB] United Kingdom ............... 8914563

[51] Int. Cl.⁶ ..................... G01N 33/53; C09K 3/00
[52] U.S. Cl. ................... 252/700; 435/5; 435/6; 435/7.1; 435/7.92; 435/7.93; 435/7.94; 435/7.95; 435/968; 435/973
[58] Field of Search ................ 252/700; 435/5, 435/6, 7.1, 7.92–7.95, 8, 26, 968, 973

[56] References Cited

U.S. PATENT DOCUMENTS

| 4,931,223 | 6/1990 | Bronstein et al. | 252/700 |
| 5,340,714 | 8/1994 | Katsilometes | 435/6 |

OTHER PUBLICATIONS

Newman et al., Synthesis and Properties of 4,5-Dimethylacridine and 1,4,5,8-Tetramethylacridine, J. Org. Chem., 26:812–815 (1961).

Seitz, Immunoassay Labels Based on Chemiluminescence and Billuminescence, Clin. Biochem., 17:120–126 (1984).

Weeks et al., Acridinium Esters as High Specific Activity Labels in Immunoassays, Clin. Chem., 29:1474–1478 (1983).

Primary Examiner—Philip Tucker
Attorney, Agent, or Firm—Carlos A. Fisher; Richard Weerburg

[57] ABSTRACT

A method for the assay, detection etc. of each of a plurality of substances of interest in a sample comprises labelling each of the substances with one or more components each capable of taking part in a respective distinguishable chemiluminescent reaction. Luminescent reagents for use in the method are also disclosed.

29 Claims, 2 Drawing Sheets

DETECTING OR QUANTIFYING MULTIPLE ANALYTES USING LABELLING TECHNIQUES

This is a continuation of application Ser. No. 07/781,182 filed on May 26, 1992, now abandoned.

BACKGROUND OF THE INVENTION

This invention relates to methods and reagents for the assay, detection, quantification, location or analysis of each of a plurality of substances of interest ("analytes") in a sample in which each substance is linked ("labelled") with another molecule or molecules capable of taking part in a chemiluminescent reaction.

For the purposes of this specification, a chemiluminescent reaction is defined as one which involves a chemical reaction that results in the emission of electro-magnetic radiation. This luminescence is to be distinguished clearly from fluorescence and phosphorescence. Here, luminescence, or more precisely, chemiluminescence also encompasses light emission from biological reactions (bioluminescent reactions).

A luminescent reaction is normally one between at least two molecules (S and L) with or without other reagents, cofactors, or a catalyst (D) or under the influence of a physical trigger. L is the substance which generates light, such as luminol. S is the substance which reacts with L to cause excitation, for example oxygen or hydrogen peroxide. D (if present) is a colactor, and/or catalyst or trigger such as an enzyme, a luciferass, or potassium ferricyanide. The reaction between L and S results in the conversion of L to an excited molecule L* and the return of this excited molecule to a non-excited state results in the emission of a photon. The reaction between L and S and the decay of L* to the non-excited state may take place spontaneously or may require the presence of the cofactor or catalyst D, or a physical trigger such as temperature. An example of such a reaction is the oxidation by $H_2O_2$ of luminol. The catalyst and cofactors are often inorganic compounds as here, but may also be extracted from biological material such as the enzyme peroxidase which catalyses the luminescent reaction involving luminol.

These methods and reagents discussed above may be used in a wide variety of techniques such as immuno-assays, protein binding assays, nucleic acid hybridisation assays, cellular receptor binding assays and other analogous techniques which involve binding of the substance of interest with a specific binding partner or reagent. These types of linking are referred to herein as "binding or otherwise linking with".

The substances of interest may be peptides, proteins, polypeptides, nuCleic acids and other substances of biological interest.

Binding assays have been used for many years in the quantitation of molecules of biological interest. Numerous examples have been described in which the binding step is an immunological reaction, a protein binding reaction, reaction with a cellular receptor or a complementary nucleic acid hybridization reaction. Sensitive assays based on these reactions require the use of a label which can be attached or incorporated into one of the binding partners of such a reaction such that the degree of binding and hence the concentration or mass of another component of the reaction—the substance of interest—can be determined. Many variations of the basic binding reactions have been described and many different labels used, including radioisotopes, enzymes, fluorescent molecules and chemiluminescent molecules.

Various combinations of these have been used in sequence for the detection and quantitation of a wide variety of analytes ranging from small molecules such as hormones and drugs to large molecules such as nucleotides.

Generally speaking, these techniques have only been applied to the investigation of a single analyte in one test reaction, but there have been a limited number of examples where two analytes have been determined essentially using a single test procedure. The best known of these have been simultaneous immunoassays and/or protein binding assays for vitamin B12 and folic acid and also for thyroxine and thyro-trophin. In these cases the two different reactions are monitored independently using a different radioactive isotope for each. Here use is made of cobalt-57 and iodine-125 whose radioactive emissions are distinguishable using an appropriate gamma counter. Similar strategies have also been used for the simultaneous determination of lutrophin and follitrophin.

Radioactive reagents have three major disadvantages. Firstly, the method of labelling involves the use of highly radioactive and hence potentially hazardous reagents. Secondly, the shelf life of the radioactively labelled substance is often relatively short not only because by its very nature the radioactive isotope is continuously decaying, but also radioactively labelled proteins are often unstable. Thirdly, it is often difficult to label proteins sufficiently to provide a sensitively and rapidly detectable reagent. The measurement of luminesence is both highly sensitive and very rapid, the time of measurement being of the order of seconds rather than the several minutes normally required for measurement of radioactivity. The attachment either covalently or non-covalently, to substances not normally capable of taking part in a luminesescent reaction of a substance which is capable of taking part in a luminescent reaction provides a reagent which can be rapidly measured in very small quantities.

Work has been described relating to the use of different fluorescent molecules in so-called "dual labelling" systems. However, fluorescent labelling systems are usually capable of only gross analysis of substances and are not generally suitable for sensitive analysis. Also, with fluroescent systems, the sample is illuminated by U.V. radiation to measure the fluoresence and this may cause major problems due to photobleaching. Multiple analyte immunoassays based on the use of fluorophores have been described in which the different labels used have been chelates of different lanthanide metals emitting at different wavelengths. Limitations arise here because certain of the fluorophores used have low quantum yields and generally all assays based on these materials require complex instrumentation and chemistries in order to achieve the high levels of performance which are characteristic of many chemiluminescent systems (Ref.1).

SUMMARY OF THE INVENTION

Broadly stated, according to one aspect of this invention, there is provided a method for the assay, detection, quantification, location or analysis of each of a plurality of substances of interest contained in a sample, which comprises labelling each of said substances with one or more components capable of taking part in a respective distinguishable chemiluminescent reaction.

In another aspect, this invention provides a method for the assay, detection, quantification, location of analysis of a sample containing at least two substances of interest which comprises:

(i) treating said sample to form at least first and second complexes, said first complexes being made up of one of said substances, or a respective associated substance, bound or otherwise linked with a first reagent capable of taking part in a first chemiluminescent reaction and said second complexes being made up of another of said substances, or a respective associated substance, bound or otherwise linked with a second reagent capable of taking part in a second chemiluminescent reaction which has emission characteristics distinguishable from those of said first chemiluminescent-reaction;

(ii) subsequently treating said sample containing said first and second complexes to cause said first and second chemiluminescent reactions to occur, and (iii) observing, sensing, measuring and/or recording the emission of each of said chemiluminescent reactions.

In yet another aspect, this invention provides a luminescent reagent which comprises a mixture of at least two substances capable of binding or otherwise linking with respective different binding partners, one of said substances being labelled with one or more components capable of taking part in a respective one chemiluminescent reaction and another of said substances being labelled with one or more components capable of taking part in a respective other chemiluminescent reaction of which the emission characteristics are distinguishable from said one chemiluminescent reaction.

We have found that different chemiluminescent labels can be produced which, by appropriate chemical manipulation, possess different characteristics in terms of the speed and wavelength of light emission and that these different labels can be used advantageously in analyte binding systems to permit the substantially simultaneous quantitation of two or more different analytes within a single test procedure.

It is known that certain changes in the structure of chemiluminescent molecules cause changes in the spectrum of the emitted light. Recently it has been suggested that conventional enzyme immunoassays with light emitting end points could be used for multiple assays (Ref.2) though it is not taught how this may be achieved nor is it obvious how such assays would be performed. Neither there any data to support this suggestion. No comparable suggestions have been made for situations in which luminescent molecules themselves are linked to substances of biological interest as opposed to using luminescent end-point enzyme immunoassays. The advantages of using such direct labelling as opposed to enzymic modulation are well established and yield advantages in terms of simplicity, robustness and sensitivity. No teachings exist as to how the advantages of such systems may be exploited for multiple analyte assays nor is it obvious what instrumentation would be required etc. in order to perform such assays. More recently it has been shown that modification of the luciferase component of bioluminescent reactions by genetic manipulation (Ref.3) forms an additional means of modifying the wavelength of emission from such reactions as an alternative to modifying the chemical structure of the corresponding luciferin.

In a further aspect it is known that, generally, change in chemical reaction conditions or structural changes within the reactant molecules themselves may affect the rates of their various possible reactions. Similarly, more specifically, the kinetics of chemiluminescent reactions are often affected by the chemiluminescent molecule. It has been suggested for example (Ref.4,5) that the rates of chemiluminescent reactions of acridinium salts are dependent on certain structural features. Likewise it has been reported that enzyme driven-chemiluminescent reactions may be affected by the structure of the substates (Ref.6). That these kinetic effects may be utilised in the development of multiple assays based on such kinetic differences has not been taught, neither is it obvious from any related art how such assays may be configured and utilised.

BRIEF DESCRIPTION OF THE DRAWINGS

A discussion of non-limiting embodiments of the invention now follow, together with a specific example of an assay procedure.

DETAILED DESCRIPTION OF THE INVENTION

Figure 1:
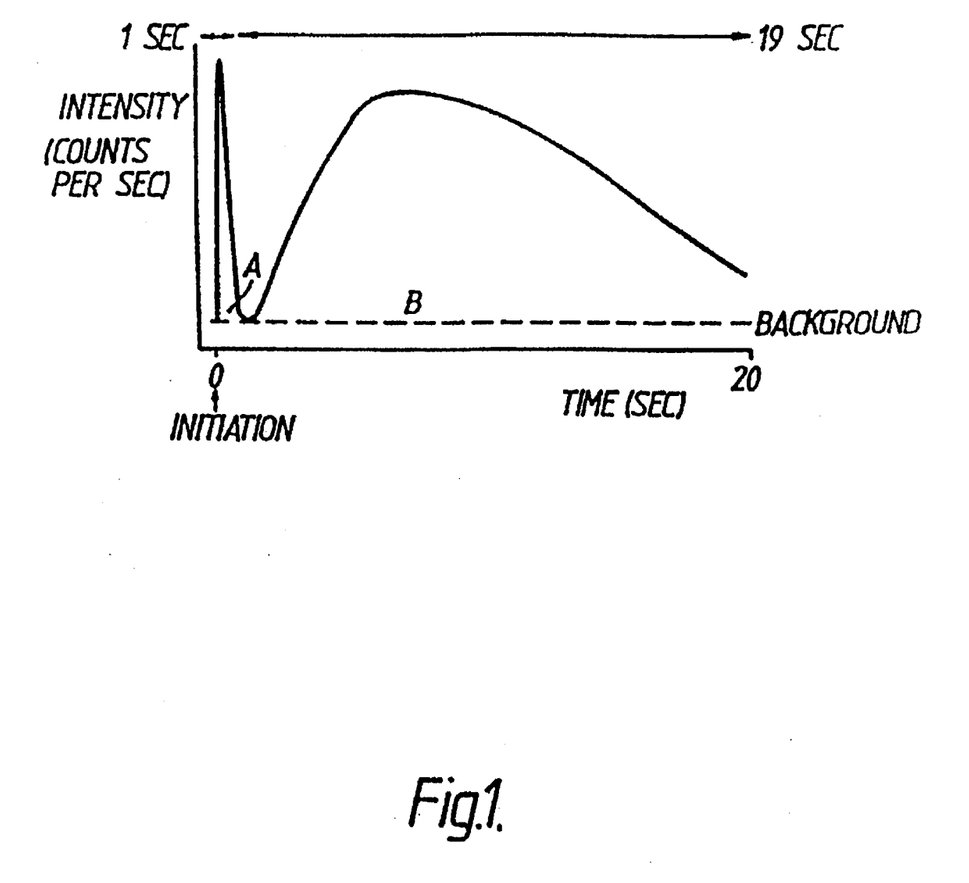
FIG. 1 is a schematic graph showing emission intensity vs. time a typical test procedure according to the invention.

A and B are the analytes of interest and are each capable of binding more than one antibody molecule so that parallel two-site immunoassays can be set up. A mixture of antibodies capable of binding A and B is coated on to the walls of a test tube. The sample for analysis containing unknown amounts of A and B is added to the tube together with a mixture of soluble complementary antibodies capable of binding to other sites on A and B. The soluble anti-bodies specific for A and B are labelled with chemiluminescent molecules exhibiting distinguishable characteristics, e.g. fast and slow light emission. Following an appropriate incubation period, two-site immune complexes will be formed on the sides of the tube, the extent of immune complex formation depending on the amount of A and B present. Following removal of unbound substances by aspiration of the soluble contents of the tube, the chemiluminescence emission remaining is triggered and then measured in a luminometer. The total number of photons emitted is proportional to the total amount of A and B present. However, in this example, the chemiluminescence emission from labelled antibodies specific for A is rapid and complete within one second whereas the emission from labelled antibodies specific for B is much slower and reaches a peak after initiation before decaying over the next nineteen seconds (see FIG. 1). Thus measurement of the photons emitted in two separate time windows of 1 and 19 seconds within an overall measuring time of 20 seconds permits independent quantitation of A and B upon calibration of the system.

ASSAYS TECHNIQUES AND ANALYTES

The methods in accordance with the invention may quantify those species of biological interest which are identifiable using single analyte quantitation techniques. The following examples are given with guidance as to the type of binding reaction used. This list is given for example only and does not imply any limitations of the invention:

1. IMMUNOASSAYS

Drugs, vitamins, steroids, thyroid hormones, peptides, polypeptides, proteins, immuno-globulins, viruses, bacteria, protozoa.

2. PROTEIN BINDING ASSAYS

Vitamins, cofactors, enzyme inhibitors.

3. NUCLEIC ACID HYBRIDIZATION ASSAYS

Oligonucleotides, polynucleotides, DNA, RNA, onocogenes, microorganisms.

4. RECEPTOR BINDING ASSAYS

Progestogen receptors, estrogen receptors, thyrotrophin receptors, thyroid hormone receptors.

Certain pairs of groups of analytes are often measured to get a more complete picture of the biological system or to improve efficiency of testing of the biological system. In such cases the availability of simultaneous, multi-analyte measurement offered by the invention is uniquely advantageous. Examples of such groups of analytes are given below but do not imply limitations of the invention.

1. HORMONES

Thyroxin/thyrotrophin, lutrophin/follitrophin, adrenocorticortrophin/cortisol.

2. VITAMINS AND COFACTORS

Vitamin B12/folic acid, 1,25-dihydroxycholical-ciferol/25-hydroxycholecalciferol.

3. NUCLEIC ACIDS (FROM VIRUSES AND MICRO-ORGANISMS)

Neisseria Gonorrhoea/Chlamydia Trachomatis.

4. TUMOUR MARKERS

Prostate Specific Antigen/Prostatic Acid Phosphatase, alphafetoprotein/carcinoembryonic antigen/chorionic gonadotrophin.

LABELS

The preferred way of associating chemiluminesence activity with the appropriate binding reaction is to chemically or physically couple a component such as a chemiluminescent molecule, capable of taking part in a chemiluminescent reaction, to one of the components of that binding reaction so as to produce a specific labelled reagent. The luminescent reagents according to the present invention will thus include two or more such labelled reagents each carrying a label having different characteristics in terms of kinetic and/or spectroscopic properties. Each of these labelled reagents will have a particular specificity for taking part in a given binding reaction, thus each given binding reaction can be monitored independently even though two or more such reactions are occurring simultaneously. Hence it is possible to quantify, independently and simultaneously, the analytes taking part in these parallel binding reactions.

Different members of a number of classes of chemiluminescent molecules are capable of exhibiting differences in kinetic and/or spectroscopic properties and can hence be used in the invention, including acridinium and related compounds (e.g. phenanthridinium compounds), phthalhydrazides and related compounds (e.g. naphthalhydrazides), oxalate esters and related compounds and also stabilised dioxetanes and dioxetanones. The variations of compounds within such groups are well-known to those moderately skilled in the art, likewise it is known that the quantum yield, kinetics and emission wavelengths of their chemiluminescent reactions are affected by their structure (see earlier and also Refs. 7–11). Thus the structures of a plurality of compounds differing in kinetics or emission wavelength parameters, suitable for use in this invention are individually readily conceived by one skilled in the art. For example, from the existing literature, one skilled in the art would know to choose from those compounds with high quantum yields, and to choose those compounds which, relative to each other possessed substantial differences in their reaction rates or their emission wavelengths, in order to maximise the resolution between the detection of these compounds. Aryl acridinium esters may be used as labels with appropriate chemical modifications made to produce the desired kinetic and spectroscopic parameters. Some examples of such compounds are given below and do not imply any limitations of the invention.

1. KINETIC VARIATION a.

Duration of light emission under standard conditions = 0.8 seconds b.

Duration of light emission under standard conditions = 60 seconds

In the acridinium phenyl ester of 1a. the phenyl moiety is substituted with F groups which are electron withdrawing and thus modify the acridinium phenyl ester so that the emission of light occurs over a relatively short period. In the acridinium phenyl ester of 1b, the phenyl moiety is substituted with $CH_3$ groups which are electron donating so that the emission of light occurs over a relatively long period. Other electron donating and withdrawing groups may be used.

c.

Duration of light emission under standard conditions (9,10-diphenylanthracene fluorescent acceptor) = 30 min d.

Duration of light emission under standard conditions (9,10-diphenylanthracene fluorescent = 2 min

Table 1 gives further examples for the series

| $R_1$ | $R_2$ | $R_3$ | $R_4$ | $R_5$ | $R_6$ | t ½ (decayphase half-life) |
|---|---|---|---|---|---|---|
| $CH_3$ | H | H | H | H | H | 0.6 s |
| $CH_3$ | $CH_3O$ | H | H | $CH_3O$ | H | 7 s |
| $C_6H_5CH_2$ | H | H | H | H | H | 0.5 s |
| $CH_3$ | $CH_3$ | H | H | H | H | 11 s |
| $CH_3$ | $NO_2$ | H | H | $NO_2$ | H | <0.4 s |
| $CH_3$ | H | $CH_3$ | $CH_3$ | H | H | 0.7 s |
| $CH_3$ | $CH_3$ | H | H | $CH_3$ | $CH_3$ | 4 s |
| $CH_3$ | Br | H | H | Br | H | <0.4 s |

2. SPECTROSCOPIC VARIATION a.

Emission λmax ~430 nm b.

Emission λmax ~510 nm c.

Emission λmax ~430 nm d.

λmax ~520 nm e.
λmax ~430 nm f.
λmax ~512 nm

In 2b, the electronic conjugation of the nucleus has been increased so that the emission radiation is of relatively long wavelength.

In each of the acridinium compounds illustrated above, R is selected to allow covalent coupling to a component of the appropriate binding reaction. Appropriate coupling groups are well described but in this example are selected such that the desired kinetic and/or spectroscopic properties of the molecule are maintained and also that the final labelled reagent is still active in terms of its ability to participate in the binding reaction. Such groups include N-hydroxysuccinimide esters, imidate esters, isothiocyanates and other established active group or groups that can give rise to active groups to facilitate coupling to molecules of biological interest. Preferably these groups are linked to the chemiluminescent moiety by an aliphatic chain of appropriate length.

In a further aspect it is possible to also make use of chemiluminescent reactions which involve energy transfer to a fluorescent acceptor molecule. As an example of this it is possible to label an antibody of one specificity with fluorescein and an antibody of another specificity with rhodamine. These antibodies can be used in simultaneous two-site assays and the end-points determined by introduction of a peroxyoxalate chemiluminescence system (hydrogen peroxide/bis-2, 4-dinitrophenyl oxalate). Radiationless energy transfer occurs resulting in the emission of light at two different wavelengths (green-yellow from fluorescein/red from rhodamine), the intensities of the emissions are directly proportional to the amount of the relevant labelled antibody bound in the immunochemical reactions.

ANALYTE-BINDING PARTNERS (REAGENTS AND BINDING REACTIONS)

The following schemes represent examples of binding partners or binding reactions that it is possible to use for the determination of concentrations of single analytes which are used currently:

| Key: | |
|---|---|
|  | Solid phase matrix (e.g. coated tube, magnetisable particles) |
|  | Different analytes represented by A and B |
|  | Antibodies specific for A and B respectively or binding proteins specific for A and B respectively or receptors capable of binding A and B respectively |
|  | Oligonucleotide sequences A and B |
|  | Complementary oligonucleotide sequences |
|  | Binding reagent for double-stranded (recombinant) nucleic acid sequences Chemiluminescent labels exhibiting $L_1$, $L_2$ different reaction kinetics and/or spectroscopic properties respectively. |

1a. Two-Site immunoassays

Antibodies of a given specificity for the analyte recognise different parts of the given analyte to permit formation of the two-site immune complex. Excess concentrations of reagent over analyte are used in two-site systems.

1b Competitive binding immunoassays (labelled antigen)

1c Two-site/competitive binding (labelled combination

1d Two-site/competitive binding (labelled antibody) combination

It should be noted that limiting reagent concentrations are used in competitive binding systems.

2. Oligonucleotides hybridization assays

The above are all examples of heterogeneous assay systems in which the analyte/binding-partner complex is isolated from uncomplexed material. Additionally it is possible to apply the disclosed systems to homogeneous assays.

INSTRUMENTATION

Photon counting equipment may be used for the measurement of light intensity. The sensing equipment should be capable of distinguishing the emissions from the distinguishable chemiluminescent reactions.

1 A KINETIC DISCRIMINATION

As described in the earlier example, the equipment should be capable of recording measurements of light intensity (preferably as photon counts per unit time) within at least two time frames to permit independent measurement of the intensity arising from slow and fast reactions. In many instances there will be overlap between the two signals which is accounted for by appropriate selection of time frames or by mathematical estimation of the overlap.

2. SPECTROSCOPIC DISCRIMINATION

Here it is necessary to measure the intensity of two or more wavelengths simultaneously. This can be achieved, e.g. by use of the necessary number of photomultiplier tubes each fitted with a bandpass interference filter to permit measurement of one signal at the exclusion of others. Alternatively a single photomultiplier tube can be used such that the light emitted from the reaction is first passed through a fast scanning spectrometer or filter/chopper system. Synchronisation of the photomultiplier tube output with the scanning or chopping frequency thus permits independent quantitation of the different wavelengths.

SPECIFIC EXAMPLE

1. Preparation of labelled antibodies: a. 4-(2-carbonylethyl) phenyl-10-methyl acridinium 9-carboxylate fluorosulphonate labelled antibodies to human chorionic gonadotrophin (hCG).

The acridinium label was synthesized as follows: acridinium-9-carboxylic acid (5g) was refluxed with thionyl chloride (15 ml) for 3 hours. The solvent was removed under reduced pressure and the product suspended in anhydrous pyridine (35 ml). Benzyl 4-hydroxyphenylpropanoate (9 nmol) was added and the solution stirred overnight at room temperature. The mixture was subsequently poured into crushed ice/1M hydrochloric acid (250 ml) and the resulting precipitate filtered, washed with water and dried under reduced pressure. The 4-(2-benzyloxycarbonylethyl)phenyl-9-acridine carboxylate thus obtained was recrystallised from benzene/cyclohexane. 0.46 g of this was dissolved in hydrogen bromide/acetic acid mixture (45/55 w/w, 10 ml) and the solution stirred for 2 h at 50°–55° C. The solution was poured into water (100 ml) and the resulting yellow solid, filtered, washed with water and dried under reduced pressure, thence recrystallised from acetonitrile/chloroform to yield 4-(2-carboxyethyl)phenyl-9-acridine carboxylate. N-hydroxysuccinimide (62 mg) was dissolved in dimethylformamide (5 ml) together with 200 mg of the above acridine carboxylate. The mixture was cooled to –20° C. and dicyclohexylcarbodiimide (123 mg) added, followed by stirring for 2 h at –20° C., thence overnight at room temperature. One drop of glacial acetic acid was then added and the mixture left for a further 30 min. The dicyclohexylurea was removed by filtration and the material obtained by evaporation of the liquor was recrystallised from benzene/cyclohexane to yield 4-(2-succinimidyloxy carbonylethyl) phenyl-9-acridine carboxylate. The product (234 mg) was dissolved in anhydrous chloroform (25 ml) and methyl fluorosulphonate (0.5 ml) added. The precipitate which formed after stirring at room temperature for 18 hours was filtered and washed with anhydrous benzene to yield 4-(2-succinimidyloxycarbonylethyl) phenyl-10-methylacridinium-9-carboxylate fluorosulphonate. Mouse monoclonal antibodies (50 µg) raised to human chorionic gonadotrophin were dissolved in sodium phosphate buffer (pH 7.4, 0.1M, 200 µl) containing 0.15M sodium chloride. A stock solution was made of the acridinium-succinimidyl ester in acetonitrile (0.5 mg/ml) and 10 µl added to the antibody solution with mixing. After incubation at room temperature for 15 min in the dark, a solution of lysine monohydrochloride (100 µl, 10 mg/ml) in the above buffer was added and the mixture left for a further 5 min. The mixture was purified on a column of Pharmacia Sephadex G25-M® (30 cm×0.6 cm) equilibrated and eluted with phosphate buffered saline (pH 6.3, 0.1M, 0.15M NaCl) containing 0.1% (w/v) bovine serum albumin and 0.005% (w/v) sodium azide. 0.5 ml fractions were collected and the void volume fractions pooled and stored at 4° C.

b. 4-(2-imidylethyl)-2,6-dimethyl-10-methylacridinium-9-carboxylate dichloride labelled antibodies to human alpha-fetoprotein (AFP).

The acridinium label was synthesised as follows: acridinium-9-carboxylic acid (2.5 g) was refluxed with thionyl chloride (10 ml) for 3 hours. The solvent was removed under reduced pressure and the product suspended in anhydrous pyridine (25 ml). 2,6-dimethyl-4-hydroxyphenylpropionitrile (1.3 g) was added and the solution stirred overnight at room temperature. The mixture was subsequently poured into crushed ice/1M hydrochloric acid (250 ml) and the resulting precipitate filtered, washed with water and dried under reduced pressure. The 4-(2-cyanoethyl)-2,6-dimethylphenylacridinium carboxylate thus obtained was dissolved in anhydrous chloroform (15 ml) and methyltrifluoromethylsulphonate (0.5 ml) added. The precipitate which formed after stirring overnight at room temperature and addition of diethylether was filtered off and washed with anhydrous benzene to yield 4-(2-cyanoethyl)-2,6-dimethyl-phenyl-10-methyl-9-acridiniumcarboxylate trifluoromethylsulphonate which was subsequently dissolved (69 mg, 10 ml) in anhydrous methanol. HCl gas was bubbled through the solution under nitrogen, kept at ice temperature for 2 hours and left to stand for a further 1 hour. The crystals formed were filtered under an atmosphere of dry nitrogen and washed with anhydrous methanol to yield 4-(2-methyloxyimidylethyl)-2,6-dimethylphenyl-10-methylacridinium-9-carboxylate dichloride. Mouse monoclonal antibodies (50 μg) raised to human alpha-fetoprotein were dissolved in sodium borate buffer (pH 9.5, 0.1M, 200 μl) containing 0.15M sodium chloride. A stock solution was made of acridinium imidoester in acetonitrile (0.5 mg/ml) and 190 μl added to the antibody solution with mixing. After incubation at room temperature for 30 min in the dark, a solution of lysine monohydrochloride (100 μl, 10 mg/ml) in the above buffer was added and the mixture left for a further 15 mins. The mixture was purified as described above.

2. Preparation of solid-phase antibodies

Monoclonal antibodies to human chorionic gonadotrophin and alpha-fetoprotein recognising distinct epitopes to those recognised by the labelled antibodies were coupled to paramagnetic particles using published methods.

3. "Simultaneous" immunochemiluminometric assay for human chorionic gonadotrophin and human alpha-fetoprotein.

Solid phase antibodysuspensions (800 μg/ml) were mixed in equal volumes. Labelled antibody solutions (10 ng/ml anti-hCG, 50 ng/ml anti-AFP) were mixed in equal volumes. Diluent buffer was same as antibody purification buffer (above). Standard mixtures for calibration consisted of solutions containing known concentrations of hCG and AFP in horse serum. 50 μl of patient serum sample were dispensed in duplicate into 12×75 mm polystyrene test tube. Standard tubes were set up in duplicate using 50 μl of the appropriate standard. 100 μl of the labelled antibody mixture were added followed by 100 μl of the solid-phase antibody mixture. The tubes were mixed and set aside for 1 hour at room temperature. 1 ml of wash solution (1.76 g/l sodium dihydrogen orthophosphate, 0.15M sodium chloride, 0.5% (W/v) sodium azide, 0.5% bovine serum albumin, 1% (v/v) RITON® X-100) was added and the tubes placed in a magnetic rack to facilitate sedimentation of the solid phase. The supernatants were decanted to waste and a further 1 ml of wash buffer added followed by mixing of the tube contents. A further sedimentation/decantation step was performed and the tubes placed in a luminometer.

4. Measurement of light intensity.

Figure 2:
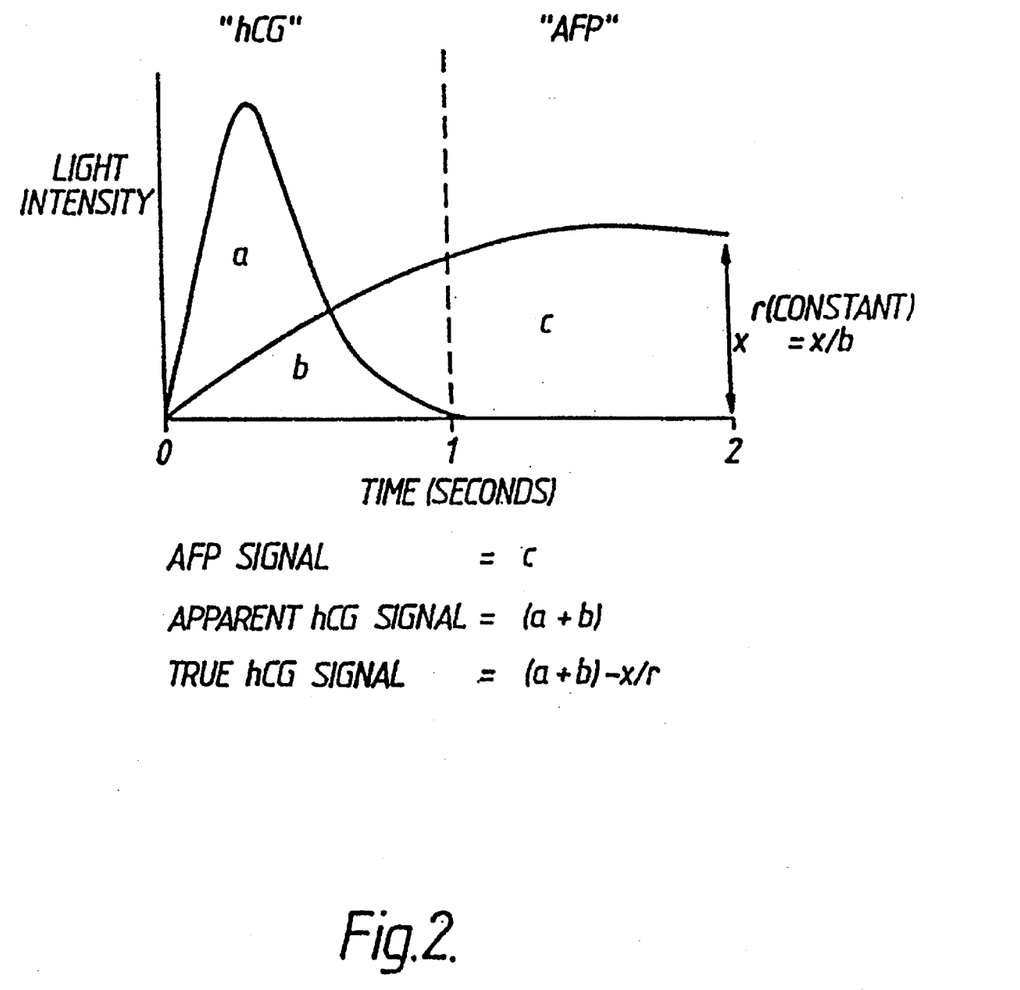
FIG. 2 is a schematic graph showing emission intensity vs. time in an example of procedure according to the invention for the immunochemiluminometric assay for human gonadotrophin and human alpha-fetoprotein.

Measurements of light emission were made in a Ciba Corning Magic Lite Analyzer using procedures recommended by the Manufacturer. Manipulation of the software enabled distinct, sequential integration of light intensity with respect to time. Separate integrations were performed in the ranges 0–1 and 1–2 seconds corresponding to light emission from the hCG and AFP antibodies respectively and hence being proportional to the concentrations of hCG and AFP in the sample. Since some overlap existed due to interference with the hCG signal by the AFP signal, correction was necessary. This was achieved by estimating the AFP contribution to the 0–1 second integration using the previously determined relationship of the light intensity at seconds to the integral between 0–1 seconds, as can be seen in FIG. 2.

| [hCG] U/L | Photon Counts | [AFP] kU/L | Photon Counts | Overlap | Corrected hCG Photon Counts |
|---|---|---|---|---|---|
| 250 | $1.22 \times 10^6$ | 250 | $1.14 \times 10^5$ | $3.35 \times 10^4$ | $1.19 \times 10^6$ |
| 125 | $8.11 \times 10^5$ | 125 | $7.4 \times 10^4$ | $2.18 \times 10^4$ | $7.89 \times 10^5$ |
| 62.5 | $4.66 \times 10^5$ | 62.5 | $4.2 \times 10^4$ | $1.24 \times 10^4$ | $4.54 \times 10^5$ |
| 31.3 | $2.63 \times 10^5$ | 31.3 | $2.3 \times 10^4$ | $6.76 \times 10^3$ | $2.56 \times 10^5$ |
| 15.6 | $1.33 \times 10^5$ | 15.6 | $1.3 \times 10^4$ | $3.82 \times 10^3$ | $1.29 \times 10^5$ |
| 0 | $3.37 \times 10^3$ | 0 | $6.6 \times 10^2$ | $1.94 \times 10^2$ | $3.18 \times 10^3$ | r = 3.40

When [hCG]>>[AFP] the residual hCG signal during the second time window made a significant contribution hence perturbing measurement ×. This was not a problem in practice and could be minimised by relative assay optimisation e.g. by manipulation of specific activities of the labelled antibodies.

In situations where accuracy is required even at extreme relative concentrations mutual overlap is accounted for by the use of more complex software capable of iterative or simulatenous equation calculation.

Where overlap is a serious problem alternative labels must be sought that exhibit greater differences in their relative kinetic properties.

REFERENCES

1. I- Hemmilä, S. Holttinen, K. Pettersson, T. Lövgren Clinical Chemistry 33 (1987) 2281
2. B. Edwards, A. Sparks, J. C. Voyta, I. Bronstein Journal of Bioluminescence and Chemiluminescence 5 (1990) 1
3. K. V. Wood, Y. A. Lam, W. D. McElroy, H. H. Seliger Journal of Bioluminescence and Chemiluminescence 4 (1989) 31
4. F. Mccapra, Accounts of Chemical Research 9 (1976) 201
5. F. McCapra, et al, Journal of Bioluminesence and Chemiluminescence 4 (1989) 51
6. B. Edwards, A. Sparks, J. C. Voyta, I. Bronstein Journal of Bioluminescence and Chemiluminescence 5 (1990) 1
7. M. M. Rauhut, L. J. Ballyky, B. G. Roberts, et al, Journal of the American Chemical Society 89 (1967) 6515.
8. K. D. Gundermann, Topics in Current Chemistry 46 (1974) 61.
9. U.S. Pat. No. 3,689,391 (Ullman).
10. U.S. Pat. No. 4,277,437 (Maggio).
11. U.S. Pat. No. 3,817,837 (Rubenstein)

The subject matter listed above is incorporated herein by reference

We claim:

1. A specific binding assay for two or more individual analytes in a liquid test sample which assay comprises:
   a) contacting the sample with two or more specific labeled reagents, wherein each such reagent comprises
      i) a member of a specific binding pair to which an individual analyte is a member, and
      ii) a different, specific light-emitting label covalently or non-covalently joined to said member, in order to form at least one labeled said specific binding pair,
   b) physically or chemically differentiating each said labeled specific binding pair from said labeled reagents, c) generating and measuring light emission from each specifically labeled specific binding pair, as a measure of the presence or amount of each said analyte, wherein each of the labels emit light at distinguishable emission maxima, or emit peak energy at distinguishable times after the generation of said emission, from at least one other of said labels.

2. The method of claim 1 wherein at least one of said labels is selected from the group consisting of acridinium compounds, phenanthridium compounds, phthalhydrazides, oxalate esters, dioxetanes and dioxetanones.

3. The method of claim 2 wherein at least one label forms an acridone before light is emitted from said label.

4. The method of claim 2 wherein at least one of said labels is an aryl acridinium ester.

5. The method of claim 4 wherein the aryl ring of at least one said label or labels is substituted at one or more position with a chemical group, each independently selected from the group consisting of an electron-withdrawing group and an electron-donating group such that emission of light occurs over said distinguishable times.

6. The method of claim 4 wherein the acridinium ring of at least one said label or labels is substituted at one or more position with a chemical group, each independently selected from the group consisting of an electron-withdrawing group and an electron-donating group such that emission of light occurs over said distinguishable times.

7. The method of claim 5 or 6 wherein said electron-withdrawing group is a halogen.

8. The method of claim 5 or 6 wherein said electron-donating group is selected from the group consisting of a methyl group and a methoxy group.

9. The method of claim 2 wherein at least one of said labels is an optionally substituted diphenylanthracene.

10. The method of claim 1 wherein at least one of said labels is a fluorescent molecule which is able to emit light by energy transfer from another molecule.

11. The method of claim 1, 4, 5, or 6 wherein each said specific binding partner is selected from the group consisting of hormones, vitamins, co-factors, nucleic acids, antigens, antibodies, haptens, ligands, enzymes, and enzyme substrates.

12. The method of claim 1, 4, 5 or 6 wherein the labels comprised in at least two of said different specific labeled specific binding pairs are caused to emit light at substantially the same time.

13. The method of claim 1 or 4 wherein the intensity of the light emitted from said labeled specific binding pairs is detected over different time intervals which may overlap in relation to the starting point of said detection and the duration of said light emission.

14. The method of claim 1 or 4 wherein the light emitted from at least two said labeled specific binding pairs is detected over different wavelength ranges.

15. The method of claim 1 or 4 wherein said sample is contacted with at least three specific labeled reagents, wherein light emitted by labels joined to at least two said reagents can be distinguished by detection over different wavelength ranges, and light emitted by labels joined to at least two said reagents can be distinguished by variation of light intensity over time.

16. The method of claim 1 wherein said light emissions are filtered by different light filtering means, said means filtering light over different wavelength ranges, and the filtered light is detected.

17. The method of claim 4 wherein a first of said different labels is an acridinium ester substituted with electron withdrawing groups and a second of said different labels is an acridinium ester substituted with electron donating groups, and wherein, upon simultaneous induction of light emission from said labels, light emission from the first label occurs over a period of time in excess of light emission from said second label, wherein said groups are selected such that emission of light occurs over said distinguishable times.

18. The method of claim 4 wherein, upon induction of light emission from said labels, a first of said different labels is an acridinium ester which emits light at a first wavelength and a second of said different labels is an acridinium ester having a greater degree of electronic conjugation than said first label, which emits light at a second wavelength longer than the first wavelength.

19. The method of claim 18 wherein said first label emits maximum light in a wavelength range of from 400 to 500 nm and said second label emits maximum light in a wavelength range of from 500 to 700 nm.

20. The method of claim 1 or 4 wherein each said label is covalently or non-covalently joined to said specific binding partner.

21. The method of claim 4 wherein two or more of said different labels are each an aryl acridinium ester.

22. The method of claim 4 wherein each said specifically labeled specific binding pairs comprise analyte bound to a specific binding partner by an interaction selected from the group consisting of an immunoassay binding reaction, a receptor binding reaction and a nucleic acid hybridization reaction.

23. The method of claim 1 wherein at least two of said specific labeled reagents individually comprise a chemiluminescent label.

24. A kit for the detection of more than one analyte in a test sample comprising two or more specifically labeled reagents, each said reagent comprising
   (i) a member of a specific binding pair to which an individual analyte is a member, and
   (ii) a different, specific label covalently or non-covalently joined to said binding pair member, said label being detectable by the emission of light from said label,
wherein each of the labels emit light at separate and distinct emission maxima, or emit peak energy at separate and distinct times after the generation of said emission, from at least one other of said labels, and wherein upon contacting said reagents with a test sample containing said analytes, the presence or amount of each said analyte is determined after the initiation of light emission.

25. The kit of claim 24 wherein each of said labels is independently selected from the group consisting of acridinium compounds, phenanthridium-compounds, phthalhydrazides, oxalate esters, dioxetanes and dioxtaetanones.

26. The kit of claim 25 wherein two or more of said different labels are each an aryl acridinium ester.

27. The kit of claim 24 wherein said binding pair member is selected from the group consisting of a nucleic acid and a protein.

28. The kit of claim 26 wherein a first of said different labels is an acridinium ester substituted with electron withdrawing groups and a second of said different labels is an acridinium ester substituted with electron donating groups, and wherein, upon simultaneous induction of light emission from said labels, light emission from the first label occurs over a period of time in excess of light emission from said second label, wherein said groups are selected such that emission of light occurs over said distinguishable times.

29. The kit of claim 24 wherein, upon induction of light emission from said labels, a first of said different labels is an acridinium ester which emits light at a first wavelength and a second of said different labels is an acridinium ester having a greater degree of electronic conjugation than said first label, which emits light at a second wavelength longer than the first wavelength.

* * * * *